United States Patent [19]
Brittain et al.

[11] Patent Number: 5,189,031
[45] Date of Patent: Feb. 23, 1993

[54] UREA DERIVATIVES, COMPOSITIONS AND USE

[75] Inventors: David R. Brittain, Rochdale; Steven P. Brown; Anthony L. Cooper, both of Cornwall; Jethro L. Longridge, Macclesfield; Jeffrey J. Morris, Sandbach; John Preston, Knutsford; Linda Slater, Macclesfield, all of England

[73] Assignee: Imperial Chemical Industries PLC, London, England

[21] Appl. No.: 831,434

[22] Filed: Jan. 5, 1992

[30] Foreign Application Priority Data

Aug. 2, 1990 [GB] United Kingdom ............... 9016984

[51] Int. Cl.$^5$ .................... A61K 31/17; C07C 317/26
[52] U.S. Cl. ................................. 514/155; 514/596; 564/49
[58] Field of Search .................. 564/49; 514/155, 596

[56] References Cited

FOREIGN PATENT DOCUMENTS 1120667 7/1968 United Kingdom .

Primary Examiner—Robert W. Ramsuer
Attorney, Agent, or Firm—Cushman, Darby & Cushman

[57] ABSTRACT

The invention concerns novel (oxamido- and ureido-phenylsulfonyl)nitromethane derivatives and pharmaceutically acceptable salts thereof which are inhibitors of the enzyme aldose reductase and are of value, for example, in the treatment of certain peripheral effects of diabetes and galactosemia. Also disclosed are pharmaceutical compositions containing one of the derivatives and processes for the manufacture and use of the derivatives.

7 Claims, No Drawings

UREA DERIVATIVES, COMPOSITIONS AND USE

This is a division of application Ser. No. 07/738,436, filed Jul. 31, 1991, now U.S. Pat. No. 5,110,808.

This invention concerns novel aniline derivatives and, more particularly, novel ureido and oxamido benzene derivatives, which are inhibitors of the enzyme aldose reductase and which are of value, for example, in the treatment of certain peripheral effects of diabetes or galactosemia. A method of treating one or more of such peripheral effects using a novel aniline derivative and pharmaceutical compositions containing such a derivative are also provided. In addition, the invention concerns novel processes for the manufacture of the novel derivatives and for the preparation of medicaments containing any of the said derivatives.

The enzyme aldose reductase is responsible for the catalytic conversion of aldoses, such as glucose and galactose, to the corresponding alditols, such as sorbitol and galactitol respectively, in warm blooded animals such as man. Alditols penetrate cell membranes poorly and, once formed, tend to be removed only by further metabolism. Consequently, alditols tend to accumulate within cells where they are formed, causing a rise in internal osmotic pressure which may in turn be sufficient to destroy or impair the function of the cells themselves. In addition, raised alditol levels may result in abnormal levels of their metabolites which may themselves impair or damage cellular function. The enzyme aldose reductase has a relatively low substrate affinity and is generally only effective in the presence of relatively large concentrations of aldose. Such large concentrations are present in the clinical conditions of diabetes (excessive glucose) and galactosemia (excessive galactose). Consequently, aldose reductase inhibitors are useful in the reduction or prevention of the development of those peripheral effects of diabetes or galactosemia which may be due in part to the accumulation of sorbitol or galactitol, respectively, in tissues such as the eye, nerve and kidney. Such peripheral effects include, for example, macular oedema, cataract, retinopathy, neuropathy and impaired neural conduction.

Although a number of aldose reductase inhibitors have been discovered and clinically evaluated, there is a continuing need for alternative inhibitors. In our European patent application, publication number 304,190, there is described a series of (phenylsulfonyl)nitromethane derivatives as inhibitors of the enzyme aldose reductase. We have now discovered that a specific group of novel ureido and oxamido benzene derivatives set out below are potent inhibitors of aldose reductase and this is a basis for the present invention.

According to the invention there is provided a novel derivative of the compound (4-amino-2,6-dimethylphenylsulfonyl)nitromethane having the formula I (set out hereinafter together with the other chemical formulae assigned Roman numerals) wherein Q is an amino group of the formula $R^1R^2N-$ or a carbamoyl group of the formula $R^3R^4N.CO-$, in which groups $R^1$ and $R^2$ are independently (1-4 C)alkyl, allyl or phenyl, the latter optionally bearing a (1-4 C)alkyl or (1-4 C)alkoxy substituent, and $R^3$ and $R^4$ are independently (1-4 C)alkyl, allyl, or benzyl, the latter optionally bearing 1 or 2 halogeno substituents; benzyl, halogenobenzyl or allyl, or together with the adjacent nitrogen atom constitute a pyrrolidine, piperidine or morpholine ring, which ring may optionally bear one or two independently selected (1-4 C)alkyl substituents; or a pharmaceutically acceptable salt thereof.

It will be appreciated that, depending on the nature of the substituents, the compounds of formula I may contain one or more chiral centres and may exist and be isolated in one or more racemic and enantiomeric forms. It is to be understood that the present invention includes any one of such forms which possesses useful effects as an inhibitor of the enzyme aldose reductase, it being well known in the art how to prepare individual enantiomers (for example, by synthesis from chiral intermediates or by separation of racemic forms, for example by chromatography on a chiral absorbent) and how to assess their efficacy as aldose reductase inhibitors (for example, by the test procedures described hereinafter).

In this specification it is to be understood that generic terms such as "alkyl" include all isomeric possibilities i.e. both straight and branched chain forms. However, individual radical names such as "propyl" are specific to the form indicated i.e. the straight chain form, any chain branching being specifically indicated as needed.

A particular value for $R^1$ or $R^2$ when it is alkyl is, for example, methyl, ethyl, isopropyl or isobutyl, of which isopropyl is of particular interest.

A particular value for $R^3$ or $R^4$ when it is alkyl is, for example, methyl, ethyl, isopropyl or isobutyl, of which isopropyl is of particular interest.

A particular value for $R^3$ or $R^4$ when it is alkyl is, for example, methyl, ethyl, isopropyl or isobutyl, of which methyl or ethyl are of particular interest; and when it is benzyl optionally bearing 1 or 2 halogeno substituents is, for example, 2-fluorobenzyl, 4-chlorobenzyl, 2,4-dichlorobenzyl, 4-bromobenzyl or 2-fluoro-4-bromobenzyl.

A particular value for $R^1$ or $R^2$ when it is phenyl bearing an alkyl or alkoxy substituent is, for example, methylphenyl, ethylphenyl or methoxyphenyl, of which 2-methylphenyl and 4-methoxyphenyl are of particular interest.

A particular value for an optional alkyl substituent which may be present when $R^3$ and $R^4$ together with the adjacent nitrogen form a ring is, for example, methyl or ethyl.

Particular combinations of Q include, for example: dimethylamino, diethylamino, diallylamino, di-isopropylamino, di-isobutylamino, N-methylanilino, N-allylanilino, N-isopropyl-2-methylanilino, N-(4-methoxyphenyl)-4-methoxyanilino, (1-pyrrolidinyl)carbonyl, piperidinocarbonyl, (2,5-dimethyl-1-pyrrolidinyl)carbonyl, (2,6-dimethyl-1-piperidinyl)carbonyl, N,N-diethylcarbamoyl, N,N-di-isopropylcarbamoyl and N,N-di-isobutylcarbamoyl.

Additional combinations of Q include, for example: (2-methyl-1-piperidinyl)carbonyl, N,N-dimethylcarbamoyl, N-benzyl-N-methylcarbamoyl, N-(4-bromobenzyl)-N-methylcarbamoyl, N-(4-bromo-2-fluorobenzyl)-N-methylcarbamoyl and (3,5-dimethyl-4-morpholinyl)carbonyl.

A preferred group of compounds comprises those compounds of the formula I wherein Q is a carbamoyl group of the formula $R^5R^6N.CO-$ wherein $R^5$ and $R^6$ are independently ethyl or isopropyl, or together with the adjacent nitrogen form a pyrrolidine, piperidine, dimethylpyrrolidine or dimethylpiperidine ring; together with the pharmaceutically acceptable salts thereof.

Specific compounds of the invention are set out in the accompanying Examples and are provided together their pharmaceutically acceptable salts as a further feature of the invention. Of these exemplified compounds, those which are of particular interest include the compounds described in Examples 1, 2, 3, 5, 6, 14, 15 and 16, or a pharmaceutically acceptable salt thereof.

Suitable pharmaceutically acceptable salts include, for example, alkali metal (such as potassium or sodium), alkaline earth metal (such as calcium or magnesium), ammonium and aluminium salts, and salts with organic bases affording physiologically acceptable cations, such as salts with methylamine, dimethylamine, trimethylamine, piperidine and morpholine.

The novel compounds of the invention may be obtained by standard procedures of organic chemistry already known for the production of structurally analogous ureido and oxamido benzenes, for example as described in our aforementioned European patent application. Such procedures are provided as a further feature of the invention and are illustrated by the following procedures in which Q and the generic substituents therein have any of the meanings defined hereinbefore.

(a) For those compounds in which Q is a carbamoyl group of the formula $R^3R^4N.CO—$, (4-amino-2,6-dimethylphenylsulfonyl)nitromethane is acylated by reaction with a carboxylic acid of the formula $R^3R^4N.CO.CO_2H$ or a reactive derivative thereof.

Particularly suitable reactive derivatives include, for example, an acid halide (especially the acid chloride and acid bromide), anhydride or mixed anhydride of the acid of the formula $R^3R^4N.CO.CO_2H$. The acid halides may readily be obtained, for example, by reaction of a salt (such as the sodium salt) of the acid of formula $R^3R^4N.CO.CO_2H$ with an agent such as oxalyl chloride or thionyl chloride or bromide. A mixed anhydride with a (1-4 C)alkanoic acid (such as formic acid) or a hemi(1-4 C)alkyl carbonate of the acid of the formula $R^3R^4N.CO.CO_2H$ may be obtained, respectively, by reaction of a salt of the said acid with an appropriate alkanoyl halide or a (1-4 C)alkyl chloroformate (such as isobutyl chloroformate).

When a free acid of the formula $R^3R^4N.CO.CO_2H$ is used, the process is preferably carried out in the presence of a suitable condensing agent, for example, a carbodiimide such as 1,3-dicyclohexylcarbodiimide, 1,3-diisopropylcarbodiimide or 1-ethyl-3-(3-dimethylaminopropyl)carbodiimide optionally together with an N-hydroxytriazole such as 1-hydroxybenzotriazole and in a suitable solvent or diluent, for example, methylene chloride or dimethylformamide, and at a temperature in the range, for example, $-20°$ to $35°$ C. and, preferably, at or near ambient temperature. When 1-ethyl-3-(3-dimethylaminopropyl)carbodiimide is used as condensing agent, it is conveniently used in the form of a hydrohalide (such as the hydrochloride) salt and, preferably, in the presence of a suitable organic base, for example, triethylamine.

The acid of the formula $R^3R^4N.CO.CO_2H$ may also conveniently be utilised in the form of its alkali metal salt, for example, its lithium, sodium or potassium salt. In these cases a suitable condensing agent such as a carbodiimide optionally together with an N-hydroxytriazole is used as described above. However, in this case, when a 1-ethyl-3-(3-dimethylaminopropyl)carbodiimide hydrohalide is used as the condensing agent, no added organic base is required.

When a reactive derivative is used, the process (a) is generally carried out in the presence of a suitable base such as a metal carbonate, for example, potassium, sodium, lithium, calcium, barium or magnesium carbonate (of which calcium carbonate is particularly preferred) or an organic base such as triethylamine, N-methylmorpholine, N-methylpiperidine or 4-(dimethylamino)pyridine. The process is conveniently carried out in a suitable solvent or diluent such as dioxan, N,N-dimethylformamide or methylene chloride and a temperature in the range, for example, 0° to 40° C. and, conveniently, at or near ambient temperature.

The starting amino compound, (4-amino-2,6-dimethylphenylsulfonyl)nitromethane, may be made by any of the general methods described in our aforesaid European patent application or as illustrated in the accompanying Examples. The starting acids of the formula $R^3R^4N.CO.CO_2H$ and their reactive derivatives may be obtained by procedures already established for structurally analogous oxamic acids and as illustrated in the accompanying Examples.

(b) For those compounds in which Q is a carbamoyl group of the formula $R^3R^4N.CO—$, N-(3,5-dimethyl-4-[nitromethylsulfonyl]phenyl)oxamic acid or a reactive derivative thereof is reacted with an amine of the formula $R^3R^4NH$.

It will be appreciated that process (b) is closely related to process (a) and that in general similar reaction conditions may be employed. Thus, for example, when a free oxamic acid is used it is generally necessary to use a suitable condensing agent such as a carbodiimide under the conditions specified in process (a) above. Similarly, particularly suitable reactive derivatives include lower alkyl esters (such as the methyl and ethyl esters) as well as those reactive derivatives mentioned in process (a) above, of which the acid chloride or bromide of N-(3,5-dimethyl-4-[nitromethylsulfonyl]-phenyl)oxamic acid are particularly preferred. Process (b) is generally performed in a suitable solvent or diluent such as 1,2-dimethoxyethane, t-butyl methyl ether or tetrahydrofuran and at a temperature in the range, for example, 0° to 40° C. The amine of the formula $R^3R^4NH$ is generally used in excess.

(c) For a compound of the formula I wherein Q is a group of the formula $R^1R^2N—$, 3,5-dimethyl-4-(nitromethylsulfonyl)phenyl isocyanate (or a precursor thereof) is reacted with an amine of the formula $R^1R^2NH$.

A suitable precursor of the isocyanate is, for example, the chloroformyl derivative, N-(3,5-dimethyl-4-[nitromethylsulfonyl]phenyl)carbamoyl chloride, which may conveniently be formed in situ during the reaction of (4-amino-2,6-dimethylphenylsulfonyl)nitromethane with phosgene in a suitable solvent such as toluene or xylene and at a temperature in the range, for example, 0° to 40° C. An inorganic base such as a carbonate mentioned in connection with process (a) may also conveniently be present.

The 3,5-dimethyl-4-(nitromethylsulfonyl)phenyl isocyanate starting material may be conveniently obtained from the above mentioned carbamoyl chloride precursor by carrying out the reaction of (4-amino-2,6-dimethylphenylsulfonyl)nitromethane with phosgene at a higher temperature, for example, in the range 30° to 80° C., and for a longer period.

In either case, the reaction (c) is generally carried out using an excess of the amine $R^1R^2NH$ is a suitable solvent or diluent such as 1,2-dimethoxyethane, t-butyl methyl ether, ethyl acetate or butyl acetate and at a temperature in the range, for example, 10° to 45° C.

(d) A thioether of the formula (II) is oxidised.

Suitable oxidising agents for this reaction include any of those which are well known in the art for the conversion of thio to sulfonyl groups and which are compatible with the presence of the acylamino and methyl groups which are also present as substituents on the benzene moiety. Thus, for example, hydrogen peroxide, an organic peracid (such as perbenzoic acid) or lead tetraacetate may be used. Alternatively, an alkali metal periodate (such as sodium metaperiodate), persulfate (such as potassium monopersulfate) or permanganate (such as potassium permangnate), or gaseous oxygen in the presence of a suitable catalyst such as platinum, may be employed. The oxidation is preferably carried out in a suitable conventional solvent or diluent for such oxidations, for example in acetic or propionic acid, and at a temperature in the general range, for example 0° to 80° C.

In certain cases, the corresponding sulfoxide derivative of the thioether of formula II may be formed as an isolable intermediate. The process of the invention also includes the oxidation of such a sulfoxide intermediate to the corresponding sulfone of formula I, for example, by reaction with an alkali metal permanganate (such as potassium permanganate) in a suitable solvent such as acetic acid and at a temperature in the range, for example, 20° to 80° C.

The starting thioethers of formula II may be obtained by conventional procedures of organic chemistry, for example, from a potassium or sodium salt of the corresponding thiophenol of the formula III by conversion to the corresponding thioacetic acid of the formula IV (or a (1-4 C)alkyl ester thereof, such as a methyl or ethyl ester) by reaction with chloro- or bromo-acetic acid (or a (1-4 C)alkyl ester thereof) in the presence of a suitable base. The acid IV (or a (1-4 C)alkyl ester thereof) is then reacted with a (1-5 C)alkyl nitrate and an alkali metal (1-6 C)alkane, for example propyl nitrate and butyllithium, to give the alkali metal salt of the corresponding 2-nitroacetic acid of the formula V (or of the (1-4 C)alkyl ester thereof). The acids of formula V are unstable and readily decarboxylate and acidification of the alkali metal salt of an acid of formula V allows the isolation of a thioether of formula II. An ester of an acid of formula V may be hydrolysed, for example, using aqueous base, to the acid of formula V and then acidified to produce a thioether of formula II.

The thiophenols of formula III may conveniently be obtained by N-acylation of 4-amino-2,6-dimethylbenzene thiol using an analogous procedure to process (a), (b) or (c) above. 4-Amino-2,6-dimethyl-benzene thiol may itself be obtained, for example by reaction of 3,5-dimethylaniline with thiocyanogen (generated in situ from lead(II) thiocyanate and bromine in methyl acetate) or with copper(II) thiocyanate to give 4-amino-2,6-dimethylphenyl isothiocyanate, which latter is then reduced, for example, with sodium borohydride in ethanol to the required thiol. ethanol to the required thiol.

(e) Reacting an alkali metal salt of a 4-N-acylamino-2,6-dimethylbenzenesulfinic acid of the formula VI with nitromethane and iodine in the presence of an alkali metal (1-6 C)alkoxide such as potassium t-butoxide or sodium methoxide.

The reaction is preferably carried out in the presence of a suitable polar solvent, for example, 1,3-dimethyl-3,4,5,6-tetrahydro-2(1H)-pyrimidinone (DMPU) or N,N-dimethylformamide (which are preferred), or N-methyl-2-pyrrolidone, and at a temperature in the range, for example, −30° to 20° C. and, conveniently, at about 0° C. The nitromethane is generally present in an excess.

The starting alkali metal salt may be obtained, for example, from the corresponding sulfinic acid of formula VI by reaction with the appropriate alkali metal hydroxide or (1-6 C)alkoxide, such as sodium or potassium methoxide or ethoxide. The sulfinic acid may itself be obtained by acylating 3,5-dimethylaniline, using a procedure analogous to process (a), (b) or (c) above, to give the corresponding N-acyl-3,5-dimethylaniline. The acylation is generally performed with an excess of the acylating agent in the presence of a base such as triethylamine in a suitable solvent or diluent such as t-butyl methyl ether or tetrahydrofuran and at a temperature of, for example, 10° to 40° C. and conveniently at or near ambient temperature. The N-acyl-3,5-dimethylaniline is then chlorosulfonated by reaction with chlorosulfonic acid to give the (4-N-acylamino-2,6-dimethylbenzene)sulfonyl chloride, which latter is reduced, for example, with a suitable sulfite (such as sodium sulfite) in the presence of a suitable buffer (such as sodium hydrogen carbonate) at a temperature of, for example, 60° to 90° C., to give the required (4-N-acylamino-2,6-dimethylbenzene)sulfinic acid.

Alternatively, the sulfonyl chloride may also be obtained, for example, from the appropriate 4-N-acylamino-2,6-dimethylphenyl isothiocyanate by reaction with chlorine in water, using conditions analogous to those described by Johnson et alia in *J. Amer. Chem. Soc.*, 1939, 61, 2548. The isothiocyanate may itself be obtained, for example, by reaction of the appropriate N-acyl-3,5-dimethylacylaniline with thiocyanogen (generated in situ from lead(II) thiocyanate and bromine in methyl acetate) or copper(II) thiocyanate in methyl or ethyl acetate.

Whereafter, when a pharmaceutically acceptable salt is required, a compound of formula I may be reacted with an appropriate base having a physiologically acceptable cation.

According to another aspect of the invention there is provided a pharmaceutical composition comprising a compound, of the formula I, or a pharmaceutically acceptable salt thereof, together with a pharmaceutically acceptable diluent or carrier.

The compositions of the invention may be in various conventional forms. Thus, they may be in a form suitable for oral use (for example as tablets, lozenges, hard or soft capsules, aqueous or oily suspensions, emulsions, dispersible powders or granules, syrups or elixirs), for topical use (for example as creams, ointments, gels or aqueous or oily solutions or suspensions) or for parenteral administration (for example as a sterile aqueous or oily solution for intravenous, subcutaneous, intramuscular or intravascular dosing) or as a suppository for rectal dosing.

The compositions of the invention may be obtained by conventional procedures using conventional pharmaceutical excipients, well known in the art. Thus, compositions intended for oral use may contain, for example, one or more colouring, sweetening, flavouring and/or preservative agents and may be in the form of hard gelatin capsules in which the active ingredient is mixed with an inert solid diluent, for example, calcium carbonate, calcium phosphate or kaolin, Compositions for oral use may also be in the form of soft gelatin capsules in which the active ingredient is mixed with water or an oil such as arachis oil, liquid paraffin or olive oil.

Suitable pharmaceutically acceptable excipients for use in tablet formulations include, for example, inert diluents such as lactose, sodium carbonate, calcium phosphate or calcium carbonate, granulating and disintegrating agents such as corn starch or alginic acid; binding agents such as gelatin or starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Aqueous suspensions will generally contain the active ingredient in finely powdered form together with one or more suspending agents, such as sodium carboxymethylcellulose, methylcellulose, hydroxypropylmethylcellulose, sodium alginate, polyvinylpyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Aqueous suspensions will also typically contain one or more preservatives (such as ethyl or propyl p-hydroxybenzoate, anti-oxidants (such as ascorbic acid), colouring agents, flavouring agents, and/or sweetening agents (such as sucrose, saccharin or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, or esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art. Topical formulations for administration to the eye will generally be in the form of an ointment, gel or sterile solution buffered at an ophthalmically acceptable pH, for example in the range pH 7.0–7.6.

The amount of active ingredient that is combined with one or more excipients to produce a single dosage form will necessarily vary depending upon the host treated and the particular route of administration. For example, a formulation intended for oral administration to humans will generally contain for example from 0.5 mg to 1 g of active agent compounded with an appropriate and convenient amount of excipients which may vary from about 5 to about 98 percent by weight of the total composition. Dosage unit forms will generally contain about 1 mg to about 500 mg of an active ingredient.

As stated previously, the compounds of the invention inhibit the enzyme aldose reductase and are thus of value, for example, in treating those diseases or conditions which are caused by excessive quantities of the products such as sorbitol formed in the body by processes catalysed by the enzyme aldose reductase.

The property of inhibiting the enzyme aldose reductase in vivo may be demonstrated in the following standard laboratory test:

Rats are made diabetic (as evidenced by severe glucosuria being present) by dosing with streptozotocin. The animals are then dosed daily with the test compound for one, two or five days. The animals are then sacrificed 2–6 hours after the final dose and the eye lenses and/or sciatic nerves are removed. After a standard work-up procedure the residual sorbitol levels in each tissue are determined by gas liquid chromatography after conversion to the polytrimethylsilyl derivatives. Inhibition of aldose reductase in vivo can then be assessed by comparing the residual sorbitol levels in tissues from the dosed diabetic group of rats with those of an undosed group of diabetic rats and an undosed, normal group of rats.

In a variation of the above test diabetic rats are dosed at a fixed daily oral dose for five days and then sacrificed 6 hours aftre the final dose and the reduction of sciatic nerve sorbitol assessed relative to that in control animals.

The property of inhibiting the enzyme aldose reductase may also be demonstrated in vitro. Thus, in a standard procedure partially purified aldose reductase is isolated in known manner from bovine lenses. The percentage inhibition of this enzyme's ability in vitro to catalyse the reduction of aldoses to polyhydric alcohols, and particularly to reduce glucose to sorbitol, caused by a test compound can then be determined using standard spectrophotometric methods.

In general, the majority of compounds of the invention show significant reduction of sciatic nerve sorbitol levels at a dose of 5 mg/kg or less in one of the above in vivo tests, together with an $IC_{50}$ in the above in vitro test in the order of $10^{-8}M$ to $10^{-7}M$. As an illustration, the compound of Example 2 produced an 82% reduction in sciatic nerve sorbitol levels after 5 daily oral doses of 3 mg/kg and had an $IC_{50}$ of about $6\times10^{-8}M$.

A compound of the formula I (or a pharmaceutically acceptable salt thereof) will primarily be administered systemically (generally by mouth) to a warm-blooded animal to produce a therapeutic or prophylactic effect mediated by inhibition of the enzyme aldose reductase, for example at a daily dose in the range of 1 to 40 mg/kg. In man, it is envisaged that a total daily dose in the range, for example, 15 to 800 mg. per man will be administered, given if necessary, in divided doses. However, the precise amount of the compound administered will naturally vary somewhat, for example, with the age and sex of the patient and the severity and extent of the condition being treated.

A compound of the formula I (or a pharmaceutically acceptable salt thereof) may also be administered topically, for example by direct topical administration to the tissue or organ in which inhibition of the enzyme is required, for example, to the eye. The precise amount of the compound administered will necessarily depend on the formulation used. Thus, for example, when a solution is administered, a concentration of the compound containing up to 0.01% by weight will generally be used. Similarly, when an ointment is administered a concentration of the compound of up to 2% by weight will generally be used. Topical formulations of a compound of the formula I (or a pharmaceutically acceptable salt thereof) may be administered to the eye of an animal, for example, man or dog, requiring treatment and/or prevention of diabetic cataracts or retinopathy, in a conventional manner, for example, using a drop or eyewash topical formulation.

A compound of the invention may be conveniently administered at or about the same time as one or more other agents which are known to have a useful effect in the treatment of diabetes or galactosemia, for example, a hypoglycaemic agent such as tolbutamide, chlorpropamide or glybenclamide. Any one or more such agents may also be conveniently present as an additional active ingredient in a composition according to the present invention.

Although the compounds of the invention are expected to be of use in the treatment of prophylaxis of human and animal diseases and conditions caused at least in part by elevated tissue sorbitol levels, they may be also be used whenever it is necessary to inhibit the enzyme known as aldose reductase either in vitro (for example during a research programme to discover other therapeutic agents) or in vivo (for example in plants, when it is desired to modify their development by affecting the metabolism/utilisation of aldoses).

The invention will now be illustrated by the following non-limiting Examples in which, unless otherwise stated:

(i) solvents were removed by rotary evaporation in vacuo with a bath temperature of 40°-50° C.;

(ii) all operations were carried out at room temperature, that is in the range 18°-26° C.;

(iii) column and flash chromatography was carried out on silica (Merck Art. 7736) and medium pressure liquid chromatography (MPLC) on silica (Merck Art. 9385), both materials available from E Merck and Co., Darmstadt, West Germany;

(iv) all end-products were characterised by microanalysis and NMR spectoscopy;

(v) yields are given for illustration only and are not necessarily the maximum attainable by diligent process development.

EXAMPLE 1

A solution of (4-amino-2,6-dimethylphenylsulfonyl)-nitromethane (1.5 g) in tetrahydrofuran (50 mL) was stirred and treated successively with calcium carbonate (0.62 g) and then (2,6-dimethyl-1-piperidinyl)-oxalyl chloride (1.38 g). The mixture was stirred for 12 hours and then water (50 mL) was added. The mixture was adjusted to pH 3 by the addition of 2M hydrochloric acid and extracted with ethyl acetate ($3\times50$ mL). The combined extracts were dried ($MgSO_4$) and the solvent evaporated. The residual oil crystallised on the addition of methanol. The solid was recrystallised from methanol to give N-(3,5-dimethyl-4-[nitromethylsulfonyl]-phenyl)-2-(2,6-dimethyl-1-piperidinyl)glyoxylamide (1.8 g, 71%), m.p. 192°-193° C.; microanalysis: found: C, 52.8; H, 6.1; N, 10.2%; $C_{18}H_{25}N_3O_6S$ requires: C, 52.5; H, 6.1; N, 10.2%.

The starting amino compound may be obtained as follows:

(1) N-Acetyl-3,5-dimethylaniline (obtained as a solid, 138° C., by acetylation of 3,5-dimethylaniline) is reacted with an excess of chlorosulfonic acid at 60° C., using an analogous procedure to that described in Organic Syntheses, Coll. Vol.I, at page 85, to give 4-acetamido-2,6-dimethylbenzenesulfonyl chloride as a solid [thin layer chromatographic analysis (TLC): Rf ca. 0.27 ($SiO2$: ethyl acetate/hexane 1:1 v/v)] in about 90% yield, which is used without drying or characterisation.

(2) The above sulfonyl chloride (10.95 g, 50 mmol) is added in portions to a vigorously stirred solution of sodium bicarbonate (8.4 g, 100 mmol) and anhydrous sodium sulfite (12 g, 95 mmol) in water (50 mL) at 70°-80° C. The temperature is kept at 70°-80° C. by intermittent heating. When the addition is complete, the mixture is heated and stirred at 70°-80° C. for a further hour. The mixture is then allowed to cool to room temperature during 4 hours and acidified with 2M hydrochloric acid. The precipitated solid is collected by filtration, washed with water, air dried and to give 4-acetamido-2,6-dimethylbenzenesulfinic acid, as a solid in 56-87% yield; TLC: Rf ca. 0.02 (silica: ethyl acetate). This acid is converted to its sodium salt by addition to a solution of sodium methoxide (1 equivalent) in methanol and evaporation of the resultant solution. The sodium salt is used without purification or characterisation.

(3) Nitromethane (6.72 mL, 124 mM) is added to a stirred solution of sodium methoxide (3.01 g, 55.8 mM) in N,N-dimethylformamide (DMF; 250 mL), cooled to 0° C. in an ice-bath. When the addition is complete, stirring is continued for an additional 30 minutes at 0° C. 4-Acetamido-2,6-dimethylbenzenesulfinic acid sodium salt (11.59 g, 56 mmol) is then added, followed immediately by iodine (7.2 g, 28.3 mmol). The mixture is stirred for 16 hours and allowed to attain room temperature. A concentrated solution of aqueous sodium sulfite is then added to partially decolourise the reaction mixture, which latter is then poured into water (about 1 liter) and acidified with 2M hydrochloric acid. The aqueous mixture is extracted with ethyl acetate. The combined extracts are washed with water, then with brine, and dried (MgSO$_4$). The solvent is removed by evaporation and the residue is purified by medium pressure liquid chromatography (MPLC) on silica, eluting with ethyl acetate-hexane (1:10 v/v, gradually increasing to 1:5 v/v) to give (4-acetamido-2,6-dimethylphenylsulfonyl)nitromethane as a solid, m.p. 179°–180° C. [purified by trituration with methanol] in 21% yield; NMR (d$_6$-DMSO, 200 MHz): 2.08(3H, s), 2.54(6H, s), 6.42(2H, s), 7.51(2H, s), 10.26(1H, s); microanalysis, found: C, 46.2; H, 5.0; N, 9.7%; C$_{11}$H$_{14}$N$_2$O$_5$S requires: C, 46.15; H, 4.9; N, 9.8%.

(4) (4-Acetamido-2,6-dimethylphenylsulfonyl)nitromethane (11.5 g, 40 mM) is added in one portion to a boiling mixture of concentrated hydrochloric acid (22 mL), water (110 mL) and ethanol (45 mL). The mixture is stirred at reflux until a clear solution formed (about 20 minutes) and then for a further 10 mins. The hot reaction mixture is then poured into an excess of ice-cold saturated sodium bicarbonate solution. The aqueous mixture is extracted with ethyl acetate. The combined extracts are washed with brine, dried (MgSO$_4$) and the solvent removed by evaporation to give (4-amino-2,6-dimethylphenylsulfonyl)nitromethane, as a solid, m.p. 132°–133° C. [after recrystallisation from ethanol] in 73% yield; NMR(d$_6$-DMSO, 200 MHz): 2.39(6H, s), 6.19(4H, s), 6.35(2H,s); microanalysis, found: C, 44.5; H, 4.9; N, 11.6%; C$_9$H$_{12}$N$_2$O$_4$S requires: C, 44.3; H, 4.9; N, 11.5%.

The starting acylating agent may be obtained as follows:

(1) A solution of 2,6-dimethylpiperidine (15.0 g) and triethylamine (13.4 g) in methylene chloride (125 mL) was cooled to about 5° C. and the stirred mixture was treated with ethyl oxalyl chloride (18.1 g), added dropwise over 40 minutes. The reaction mixture was stirred for 12 hours at ambient temperature. Water (200 mL) was then added. The methylene chloride layer was removed, washed with water (100 mL), dried (MgSO$_4$), and the solvent was evaporated. The residual oil was distilled reduced pressure to give 1-ethoxalyl-2,6-dimethylpiperidine (16.5 g, 58%), b.p. 101°–110° C. (0.01 mm Hg pressure).

(2) A stirred solution of 1-ethoxalyl-2,6-dimethylpiperidine (12.5 g) in ethanol (50 mL) was treated with a solution of potassium hydroxide (3.3 g) in ethanol (50 mL). The reaction mixture was left for 30 minutes and then evaporated to dryness. The resulting solid was dried under reduced pressure over phosphorous pentoxide for 12 hours. The dry potassium salt thus obtained was added gradually to stirred thionyl chloride (50 mL) cooled at about 5° C. When the addition was complete, the mixture was heated under reflux for 2 hours and then excess thionyl chloride was removed by evaporation. The residual oil was distilled (80° C. at 0.1 mm pressure in a Kugelrohr apparatus) to give (2,6-dimethyl-1-piperidinyl)oxalyl chloride as an oil (8.7 g, 73%) which was used without characterisation.

EXAMPLES 2–4

Using a similar procedure to that described in Example 1, the following compounds were obtained:

Example 2

N,N-di-isopropyl-N'-[3,5-dimethyl-4-(nitromethylsulfonyl)phenyl]oxamide obtained as a solid in 61% yield, m.p. 97°–98° C., after recrystallisation from methanol; microanalysis, found: C, 51.2; H, 6.4; N, 10.4%; C$_{17}$H$_{25}$N$_3$O$_6$S requires: C, 51.1; H, 6.3; N, 10.5%;

Example 3

N-(3,5-dimethyl-4-[nitromethylsulfonyl]phenyl)-2-(piperidino)glyoxylamide obtained as a solid in 78% yield, m.p. 169°–170° C., after recrystallisation from ethyl acetate; microanalysis, found: C, 49.4; H, 5.9; N, 10.8%; C$_{16}$H$_{21}$N$_3$O$_6$S requires: C, 49.9; H, 5.9; N, 10.8%;

Example 4

N-(3,5-dimethyl-4-[nitromethylsulfonyl]phenyl)-2-(1-pyrrolidinyl)glyoxylamide as a solid in 89% yield, m.p. 218°–219° C., after recrystallisation from methanol; microanalysis, found: C, 48.7; H, 5.3; N, 11.2%; C$_{15}$H$_{19}$N$_3$O$_6$S requires: C, 48.8; H, 5.2; N, 11.4%;

The starting acylating agents used in the above Examples had the following properties:

(for Example 2): di-isopropyloxamoyl chloride was obtained as an oil, b.p. 70°–74° C. (0.35 mm Hg pressure) in 71% yield starting from N-(ethoxalyl)di-isopropylamine, itself obtained as an oil, b.p. 96°–98° C. (0.5 mm Hg pressure) in 67% yield from ethoxalyl chloride and di-isopropylamine;

(for Example 3): piperidinoglyoxyloyl chloride was obtained as an oil, (distillable at 75° C. in a Kugelrohr apparatus at 0.1 mm Hg pressure) in 68% yield from 1-(ethoxalyl)piperidine, itself obtained as an oil, b.p. 110°–112° C. (0.5 mm Hg pressure) in 65% yield from ethoxalyl chloride and piperidine; and (for Example 4): (1-pyrrolidinyl)glyoxyloyl chloride was obtained as an oil (distillable at 75° C. in a Kugelrohr apparatus at 0.1 mm Hg pressure) in 73% yield from 1-(ethoxalyl)pyrrolidine, itself obtained as an oil, b.p. 105°–110° C. (0.3 mm Hg pressure) in 75% yield from ethoxalyl chloride and pyrrolidine.

EXAMPLE 5

(4-Amino-2,6-dimethylphenylsulfonyl)nitromethane (1.0 g) was added in portions during 10 minutes to a stirred solution of oxalyl chloride (2.0 g) in dimethoxyethane (50 mL) containing calcium carbonate (1.63 g), maintained at about 0°–5° C. The mixture was then further stirred at the same temperature for 30 minutes. Diethylamine (3.4 g) was then added dropwise during 5 minutes. When the addition was complete, the reaction mixture was allowed to attain ambient temperature and the solvent was removed by evaporation in vacuo. Water (50 mL) was then added. The solid which formed was collected by filtration and purified by chromatogaphy on silica using toluene containing increasing amounts of ethyl acetate as eluant. The solid obtained from the major fractions was crystallised first from carbon tetrachloride and then from 2-propanol to give N,N-diethyl-N'-(3,5-dimethyl-4-[nitromethylsulfonyl]-phenyl)oxamide as a solid, m.p. 128°–129° C.; microanalysis, found: C, 48.2; H, 5.5; N, 11.2%; $C_{15}H_{21}N_3O_6S$ requires: C, 48.5; H, 5.7; N, 11.3%.

EXAMPLE 6

A solution of di-isopropylamine (152 mg) in dry, ethanol free, ethyl acetate (2 mL) was added to a freshly prepared solution of 3,5-dimethyl-4-(nitromethylsulfonyl)phenyl isocyanate (405 mg) in warm dry, ethanol free, ethyl acetate (10 mL). After 16 hours, the volatile material was evaporated in vacuo. The residue was recrystallised from methanol (5 mL) to which had been added 2 drops of acetic acid and sufficient water to cause incipient turbidity in the hot solution. There was thus obtained 1,1-di-isopropyl-3-(3,5-dimethyl-4-[nitromethylsulfonyl]phenyl)urea as a white solid, m.p. 160°–161° C. (with decomposition), in 80% yield; microanalysis, found: C, 51.7; H, 6.4; N, 11.1%; $C_{16}H_{25}N_3O_5S$ requires: C, 51.7; H, 6.7; N, 11.3.

The starting isocyanate may be obtained as follows:

A solution of (4-amino-2,6-dimethylphenylsulfonyl)-nitromethane (15.0 g) in dry, ethanol free, ethyl acetate (200 mL) was added dropwise to a 20% w/v solution of phosgene in toluene which was stirred at 60–65 C. under a condenser filled with ice. When addition was complete the ice condenser was exchanged for a water condenser and the reaction mixture was stirred and heated under reflux for 16 hours. The solvent was evaporated and the residue was recrystallised from toluene using a small amount of active charcoal to decolorise the solution. There was thus obtained 3,5-dimethyl-4-(nitromethylsulfonyl)phenyl isocyanate as a yellow crystalline solid, m.p. 153°–155° C. in 91% yield.

EXAMPLES 7–13

Using a similar procedure to that described in Example 6 but starting from the appropriate amine, there were obtained:

Example 7

1,1-di-isobutyl-3-(3,5-dimethyl-4-[nitromethylsulfonyl]phenyl)urea, obtained as a solid, m.p. 153°–155° C., in 72% yield after recrystallisation from ethanol/water/acetic acid; microanalysis, found: C, 54.1; H, 7.0; N, 10.5%; $C_{18}H_{29}N_3O_5S$ requires: C, 54.1; H, 7.3; N, 10.5%;

Example 8

1-isopropyl-1-(2-methylphenyl)-3-(3,5-dimethyl-4-[nitromethylsulfonyl]phenyl)urea, obtained as a solid, m.p. 177°–178° C., in 50% yield after recrystallisation from methanol/water/acetic acid; microanalysis, found: C, 56.9; H, 5.8; N, 10.3%; $C_{20}H_{25}N_3O_5S$ requires: C, 57.3; H, 6.0; N, 10.0%;

Example 9

1-allyl-1-phenyl-3-(3,5-dimethyl-4-[nitromethylsulfonyl]phenyl)urea, obtained as a solid, m.p. 164°–165° C., in 84% yield after recrystallisation from ethanol/water/acetic acid; microanalysis, found: C, 56.8; H, 5.3; N, 10.4%; $C_{19}H_{21}N_3O_5S$ requires: C, 56.6; H, 5.3; N, 10.4%;

Example 10

1,1-diallyl-3-(3,5-dimethyl-4-[nitromethylsulfonyl]-phenyl)urea, obtained as a solid, m.p. 127°–129° C., in 92% yield after recrystallisation from methanol/water-/acetic acid; microanalysis, found: C, 52.3; H, 5.9; N, 11.5%; $C_{16}H_{21}N_3O_5S$ requires: C, 52.3; H, 5.8; N, 11.4%;

Example 11

1,1-dimethyl-3-(3,5-dimethyl-4-[nitromethylsulfonyl]phenyl)urea, obtained as a solid, m.p. 205°–206° C., in 91% yield after recrystallisation from methanol/water/acetic acid; microanalysis, found: C, 45.6; H, 5.2; N, 13.1%; $C_{12}H_{17}N_3O_5S$ requires: C, 45.7; H, 5.4; N, 13.3%;

Example 12

1,1-di-(4-methoxyphenyl)-3-(3,5-dimethyl-4-[nitromethylsulfonyl]phenyl)urea, obtained as a solid, m.p. 150°–151° C., in 74% yield after recrystallisation from ethanol; microanalysis, found: C, 57.8; H, 5.2; N, 8.3%; $C_{12}H_{17}N_3O_5S$ requires: C, 57.7; H, 5.0; N, 8.4%; and

Example 13

1-methyl-1-phenyl-3-(3,5-dimethyl-4-[nitromethylsulfonyl]phenyl)urea, obtained as a solid, m.p. 117°–118° C., in 72% yield after recrystallisation from ethanol/water/acetic acid; microanalysis, found: C, 54.4; H, 4.8; N, 11.1%; $C_{17}H_{19}N_3O_5S$ requires: C, 54.1; H, 5.1; N, 11.1%.

EXAMPLES 14–17

Using a similar procedure to that described in Example 5, the following compounds of the invention were obtained by reacting N-(3,5-dimethyl-4-[nitromethylsulfonyl]phenyl)oxamoyl chloride with the appropriate amine of the formula $R^3R^4NH$. The compounds had the following properties and showed satisfactory microanalyses:

Example 14

(R,S)-N-(3,5-dimethyl-4-[nitromethylsulfonyl]-phenyl)2-(2-methyl-1-piperidinyl)glyoxylamide obtained as a solid in 44% yield, m.p. 152°–153° C., after recrystallisation from ethyl acetate and starting from (R,S)-2-methylpiperidine;

Example 15

N-benzyl-N-methyl-N'-(3,5-dimethyl-4-[nitromethylsulfonyl]phenyl)oxamide obtained as a solid in 93% yield, m.p. 99°–101° C., after recrystallisation from ether and starting from N-(methyl)benzylamine;

Example 16

N-(3,5-dimethyl-4-[nitromethylsulfonyl]phenyl)-2-(3,5-dimethyl-4-morpholinyl)glyoxylamide (mixture of cis and trans isomers) obtained as a solid in 62% yield, m.p. 140°–141° C., after recrystallisation from ethyl acetate and starting from a cis/trans mixture of 3,5-dimethylmorpholine; and

Example 17

N,N-dimethyl-N'-(3,5-dimethyl-4-[nitromethylsulfonyl]phenyl)oxamide obtained as a solid in 43% yield, m.p. 171°–172° C., after recrystallisation from a mixture of ethyl acetate and hexane and starting from dimethylamine.

EXAMPLE 18

The following illustrate representative pharmaceutical dosage forms containing a compound of the formula I, such as is described in one of the previous examples, or a pharmaceutically acceptable salt thereof, for therapeutic or prophylactic use in humans:

| (a) Tablet I | mg/tablet |
|---|---|
| Compound | 100 |
| Lactose Ph.Eur | 182.75 |
| Croscarmellose sodium | 12.0 |
| Maize starch paste (5% w/v paste) | 2.25 |
| Magnesium stearate | 3.0 |
| (b) Tablet II | mg/tablet |
| Compound | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |
| (c) Tablet III | mg/tablet |
| Compound | 2.0 |
| Lactose Ph.Eur | 92.25 |
| Croscarmellose sodium | 4.0 |
| Maize starch paste (5% w/v paste) | 0.75 |
| Magnesium stearate | 1.0 |
| (d) Capsule | mg/capsule |
| Compound | 20 |
| Lactose Ph.Eur | 478.5 |
| Magnesium stearate | 1.5 |

The above formulations may be obtained by conventional procedures well known in the pharmaceutical art. The tablets (a)–(c) may conveniently be enteric coated by conventional means, for example to provide a coating of cellulose acetate phthalate.

CHEMICAL FORMULAE

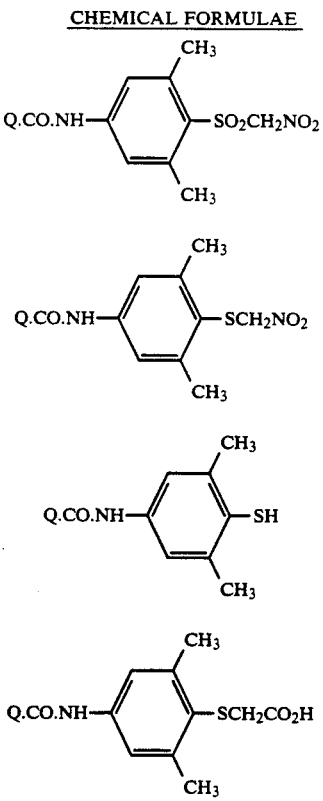

-continued
CHEMICAL FORMULAE

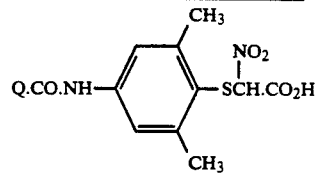

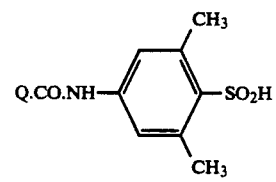

What is claimed is:

1. A derivative of the compound (4-amino-2,6-dimethylphenylsulphonyl)nitromethane having the formula I:

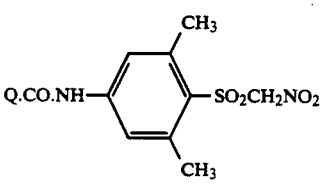

wherein Q is an amino group of the formula $R^1R^2N-$, in which $R^1$ and $R^2$ are independently (1–4 C)alkyl, allyl or phenyl, the latter optionally bearing a (1–4 C)alkyl or (1–4 C)alkoxy substituent; or a pharmaceutically acceptable salt thereof.

2. A compound as claimed in claim 1 wherein $R^1$ and $R^2$ are independently selected from methyl, ethyl, isopropyl, isobutyl, allyl, phenyl, methylphenyl, ethylphenyl and methoxyphenyl.

3. A compound as claimed in claim 1 wherein Q is selected from dimethylamino, diethylamino, diallylamino, di-isopropylamino, di-isobutylamino, N-methylanilino, N-allylanilino, N-isopropyl-2-methylanilino and N-(4-methoxyphenyl)-4-methoxyanilino.

4. A compound of the formula I selected from: 1,1-di-isopropyl-3-(3,5-dimethyl-4-[nitromethylsulfonyl]-phenyl)urea; or a pharmaceutically acceptable salt thereof.

5. A pharmaceutically acceptable salt as claimed in claim 1, which is selected from alkali metal, alkaline earth metal, ammonium and aluminium salts, and from salts with an organic base affording a physiologically acceptable cation.

6. A pharmaceutical composition which comprises a pharmaceutically effective amount of a compound of formula I, or a pharmaceutically acceptable salt thereof, as defined in claim 1, together with a pharmaceutically acceptable diluent or carrier.

7. A method of inhibiting the enzyme aldose reductase in a warm-blooded animal requiring such treatment which comprises administering to said animal an effective amount of a compound of the formula I, or a pharmaceutically acceptable salt thereof, as defined in claim 1.

* * * * *